United States Patent
Caudwell et al.

(10) Patent No.: US 7,222,671 B2
(45) Date of Patent: May 29, 2007

(54) APPARATUS AND METHOD FOR FORMATION EVALUATION

(75) Inventors: Derek Caudwell, Southampton (GB); Anthony R. H. Goodwin, Sugar Land, TX (US); Martin Trusler, London (GB); Michael W. Frels, Richmond, TX (US); Kai Hsu, Sugar Land, TX (US); Jonathan W. Brown, Dunech (GB); Julian J. Pop, Houston, TX (US); Bunker M. Hill, Sugar Land, TX (US); Andrew L. Kurkjian, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 328 days.

(21) Appl. No.: 11/021,849

(22) Filed: Dec. 23, 2004

(65) Prior Publication Data

US 2006/0137873 A1 Jun. 29, 2006

(51) Int. Cl.
*E21B 49/10* (2006.01)
(52) U.S. Cl. .................. 166/252.5; 166/264; 166/100; 166/66.5; 73/152.24
(58) Field of Classification Search ............. 166/252.5, 166/264, 100, 66.5, 65.1; 73/152.05, 152.07, 73/152.23, 152.24; 702/6, 11, 12
See application file for complete search history.

(56) References Cited

U.S. PATENT DOCUMENTS 2,590,982 A * 4/1952 Long ........................ 73/152.52
3,130,808 A   4/1964 Walker, Jr. et al.
3,346,058 A   10/1967 Bouyoucos
3,390,737 A   7/1968 Johnson
3,449,940 A   6/1969 Banks
3,608,715 A   9/1971 Snyder et al.
3,903,732 A   9/1975 Rork et al.
4,291,583 A   9/1981 Buike (Continued)

FOREIGN PATENT DOCUMENTS

EP 0282251 3/1988

(Continued)

OTHER PUBLICATIONS

Bevington, P.R. et al., "Data Reduction and Error Analysis for the Physical Sciences," McGraw Hill, 1992, pp. 161-164.

(Continued)

*Primary Examiner*—Kenneth Thompson
(74) *Attorney, Agent, or Firm*—Matthias Abrell; Kevin P. McEnaney; William Batzer (57) ABSTRACT

A viscometer for a down hole tool positionable in a well bore penetrating a subterranean formation is described. The formation contains at least one fluid therein. The down hole tool is adapted to convey at least a portion of the fluid to the viscometer. The viscometer comprises a sensor unit, and at least one magnet. The sensor unit is positionable within the down hole tool and comprises at least two spatially disposed clamps and a wire suspended in tension between the at least two clamps such that the wire is available for interaction with the fluid when the viscometer is positioned within the down hole tool and the down hole tool is positioned within the subterranean formation and receives the fluid from the subterranean formation.

32 Claims, 5 Drawing Sheets

U.S. PATENT DOCUMENTS

| | | | |
|---|---|---|---|
| 4,319,191 | A | 3/1982 | Meador et al. |
| 4,526,480 | A | 7/1985 | Ward |
| 4,574,639 | A | 3/1986 | Ward |
| 4,602,505 | A | 7/1986 | Kanda et al. |
| 4,651,101 | A | 3/1987 | Barber et al. |
| 4,655,075 | A | 4/1987 | Albert et al. |
| 4,679,427 | A | 7/1987 | Kanda et al. |
| 4,729,237 | A | 3/1988 | Suzuki et al. |
| 4,922,745 | A | 5/1990 | Rudkin et al. |
| 5,006,845 | A | 4/1991 | Calcar et al. |
| 5,048,351 | A | 9/1991 | Dames |
| 5,115,198 | A | 5/1992 | Gianzero et al. |
| 5,204,529 | A | 4/1993 | Diatschenko |
| 5,269,188 | A | 12/1993 | Esin et al. |
| 5,361,632 | A | 11/1994 | Magnani |
| 5,565,620 | A | 10/1996 | Bohlin |
| 5,622,223 | A | 4/1997 | Vasquez |
| 5,734,098 | A | 3/1998 | Kraus et al. |
| 5,741,962 | A | 4/1998 | Birchak et al. |
| 5,757,191 | A | 5/1998 | Gianzero et al. |
| 5,837,893 | A | 11/1998 | Chu |
| 6,073,492 | A | 6/2000 | Rosselson et al. |
| 6,128,949 | A | 10/2000 | Kleinberg |
| 6,147,496 | A | 11/2000 | Strack et al. |
| 6,163,155 | A | 12/2000 | Bittar |
| 6,176,323 | B1 | 1/2001 | Weirich et al. |
| 6,182,499 | B1 | 2/2001 | McFarland et al. |
| 6,336,353 | B2 | 1/2002 | Matsiev et al. |
| 6,357,536 | B1 | 3/2002 | Schrader et al. |
| 6,378,364 | B1 | 4/2002 | Pelletier et al. |
| 6,393,895 | B1 | 5/2002 | Matsiev et al. |
| 6,401,519 | B1 | 6/2002 | McFarland et al. |
| 6,494,079 | B1 | 12/2002 | Matsiev et al. |
| 6,543,281 | B2 | 4/2003 | Pelletier et al. |
| 2002/0194906 | A1 | 12/2002 | Goodwin et al. |
| 2004/0139798 | A1 | 7/2004 | Haddad et al. |

FOREIGN PATENT DOCUMENTS

| | | |
|---|---|---|
| EP | 1109016 | 6/2001 |
| EP | 1306659 | 5/2003 |
| GB | 1266939 | 3/1972 |
| GB | 2177803 | 1/1997 |
| GB | 2392980 | 3/2004 |
| WO | WO01/51898 | 7/2001 |
| WO | WO02/099414 | 12/2002 |
| WO | WO2004/068103 | 8/2004 |

OTHER PUBLICATIONS

Field Trials of the Viscosity & Fluid Density Tool (VFD) News Release; Nan Gall Technology Limited, published Aug. 2002, 1 pp. <http://www.nangall/com/products/plt/Fluid_Density_Tuned.htm;> Fluid Density (Tuned) VFD Tool; printed Dec. 10, 2004; Nan Gall Energy; pp. 1-2.

"PVT Express; Delivering Early Fluid Analysis Data;" Schlumberger pamphlet; Jun. 2003; pp. 1-5.

"Advanced Fluid Characterization; Hydrocarbon Identification and Analysis Using NMR;" Schlumberger pamphlet; Sep. 2002; pp. 1-8.

<http://www.exprogroup.com/corpus/VTFFD/vtffd.asp?Level1_ID=1;> "Vibrating Tuning Fork Fluid Density Tool;" The Expro Group; printed Nov. 23, 2004; 1 pp.

Caudwell et al., "A Robust Vibrating Wire Viscometer for Reservoir Fluids: results for toluene and n-decane;" Journal of Petroleum Science & Engineering 44 (2004); Feb. 2004; pp. 333-340.

Nikl, M., "Wide Band Gap Scintillation Materials: Progress in the Technology and Material Understanding;" Phys. Sat. Sol. 178; Jan. 2000; pp. 595-620.

Stokes, George Gabriel, "Mathematical and Physical Papers vol. 3;" Cambridge University Press 1901; pp. 1-65.

Retsina, T. et al., "The Theory of a Vibrating-Rod Viscometer;" Applied Scientific Research 43; 1987; pp. 325-346.

Retsina, T. et al., "The Theory of a Vibrating-Rod Densimeter;" Applied Scientific Research 43: 1986; pp. 127-158.

Avelino, H.M.T. et al., "Simultaneous Measurement of the Density and Viscosity of Compressed Liquid Toluene;" International Journal of Thermophysics, vol. 24, No. 2, Mar. 2003; pp. 323-336.

Tough, J.T. et al., "Viscosity of Liquid He II;" Physical Review vol. 132, No. 6, Dec. 1963; pp. 2373-2379.

Tough, J.t. et al., "Vibrating Wire Viscometer;" The Review of Scientific Instruments vol. 35, No. 10, Oct. 1964; pp. 1345-1348.

Goodwin, James et al., "A Vibrating Wire Viscometer for Measurements at Elevated Pressures;" Journal of Physics E: Scientific Instruments 1973 vol. 6; pp. 452-456.

Goodwin, J.M. et al., "The Viscosity of Pressurized He Above $T\lambda$;" Physica 76 (1974) pp. 177-180.

Caetano, F. et al., "The Viscosity of Di-Isodecylphthalate;" to be published in International Journal of Tyermophysics; pp. 1-11.

Caetano, F. et al., "Validation of a Vibrating Wire Viscometer: Measurements in the Range 0.5 to 135 mPa·s;" submitted to Journal of Chemical Engineering Data; pp. 1-20.

Caudwell, Derek, "Viscosity of Dense Fluid Mixtures;" Department of Chemical Engineering and Chemical Technology, Imperial College London; Jun. 2004; pp. 1-195.

* cited by examiner

APPARATUS AND METHOD FOR FORMATION EVALUATION

BACKGROUND OF THE INVENTION

1. Field of the Invention

The present invention relates to techniques for performing formation evaluation of a subterranean formation by a down hole tool positioned in a well bore penetrating the subterranean formation. More particularly, but not by way of limitation, the present invention relates to techniques for determining the viscosity of formation fluid drawn into and/or evaluated by the down hole tool while the down hole tool is positioned within the well bore.

2. Background of the Related Art

Well bores are drilled to locate and produce hydrocarbons. A down hole drilling tool with a bit at an end thereof is advanced into the ground to form a well bore. As the drilling tool is advanced, a drilling mud is pumped through the drilling tool and out the drill bit to cool the drilling tool and carry away cuttings. The drilling mud additionally forms a mud cake that lines the well bore.

During the drilling operation, it is desirable to perform various evaluations of the formations penetrated by the well bore. In some cases, the drilling tool may be removed and a wireline tool may be deployed into the well bore to test and/or sample the formation. In other cases, the drilling tool may be provided with devices to test and/or sample the surrounding formation and the drilling tool may be used to perform the testing or sampling. These samples or tests may be used, for example, to locate valuable hydrocarbons.

Formation evaluation often requires that fluid from the formation be drawn into the down hole tool for testing and/or sampling. Various devices, such as probes, are extended from the down hole tool to establish fluid communication with the formation surrounding the well bore and to draw fluid into the down hole tool. A typical probe is a circular element extended from the down hole tool and positioned against the sidewall of the well bore. A rubber packer at the end of the probe is used to create a seal with the wall of the well bore. Another device used to form a seal with the well bore is referred to as a dual packer. With a dual packer, two elastomeric rings expand radially about the tool to isolate a portion of the well bore there between. The rings form a seal with the well bore wall and permit fluid to be drawn into the isolated portion of the well bore and into an inlet in the down hole tool.

The mud cake lining the well bore is often useful in assisting the probe and/or dual packers in making the seal with the well bore wall. Once the seal is made, fluid from the formation is drawn into the down hole tool through an inlet by lowering the pressure in the down hole tool. Examples of probes and/or packers used in down hole tools are described in U.S. Pat. Nos. 6,301,959; 4,860,581; 4,936,139; 6,585,045; 6,609,568 and 6,719,049 and U.S. Patent Application No. 2004/0000433.

Formation evaluation is typically performed on fluids drawn into the down hole tool. Techniques currently exist for performing various measurements, pretests and/or sample collection of fluids that enter the down hole tool. Fluid passing through the down hole tool may be tested to determine various down hole parameters or properties. The thermophysical properties of hydrocarbon reservoir fluids, such as viscosity, density and phase behavior of the fluid at reservoir conditions, may be used to evaluate potential reserves, determine flow in porous media and design completion, separation, treating, and metering systems, among others.

Various techniques have been developed for determining viscosity of fluids. For example, viscometers having a bob suspended between fixation points for a torsion wire have also been proposed as described, for example, in U.S. Pat. Nos. 5,763,766 and 6,070,457. Viscometers have also been formed from vibrating objects. One such viscometer has been used in down hole applications for measuring the viscosity, density and dielectric constant of formation fluid or filtrate in a hydrocarbon producing well have been proposed. For example, International Publication Number WO 02/093126 discloses a tuning fork resonator within a pipe to provide real-time direct measurements and estimates of the viscosity, density and dielectric constant of formation fluid or filtrate within the hydrocarbon producing well. Another, having a wire clamped between two posts has been used in a laboratory environment as describe, for example in *The Viscosity of Pressurized He above $T_\lambda$*, Physica 76 (1974) 177-180; *Vibrating Wire Viscometer*, The Review of Scientific Instruments Vol. 35, No. 10 (October 1964) pgs. 1345-1348.

Despite the existence of techniques for measuring viscosity, there remains a need to provide accurate viscosity measurements down hole, and preferably without regard to the position of a sensor down hole relative to the gravitational field. It is desirable that such a system be capable of providing checks for precision and/or accuracy. It is further desirable that such a system be provided with a simple configuration adapted for use in a harsh well bore environment.

SUMMARY OF THE INVENTION

In at least one aspect, the present invention relates to a viscometer for a down hole tool positionable in a well bore penetrating a subterranean formation. The down hole tool is adapted to convey at least a portion of a fluid in the formation to the viscometer. In general, the viscometer includes a sensor unit and at least one magnet. The sensor unit is positioned within the down hole tool. The sensor unit comprises at least two spatially disposed clamps and a wire suspended in tension between the at least two clamps such that the wire is available for interaction with the fluid when the viscometer is positioned within the down hole tool and the down hole tool is positioned within the subterranean formation and receives the fluid from the subterranean formation. The at least one magnet emits a magnetic field interacting with the wire. The at least one magnet is desirably one or more permanent magnets.

In one version, the viscometer includes a signal processor in electrical communication with the wire for providing a signal to the wire, and an analytical circuit receiving feedback from the wire for determining the viscosity of the fluid when the viscometer is positioned within the down hole tool and the down hole tool is positioned adjacent the subterranean formation and receives the fluid from the formation.

The sensor unit of the viscometer can also be provided with a housing defining a channel. An inlet communicates with the channel and the wire is positioned within the channel such that the fluid engages the wire. In one version, the housing comprises a first housing member and a second housing member with the first housing member and the second housing member cooperating to define the channel. The first housing member and the second housing member are constructed of at least one conductive, preferably non-magnetic material. An insulating layer is positioned between the first housing member and the second housing member so as to electrically isolate the first housing member from the second housing member. A first terminal is coupled to the first housing member, and a second terminal is coupled to the second housing member such that the signal processor and the analytical circuit are in electrical communication with the first and second terminals. The first housing member and the second housing member cooperate to form the clamps. The channel extends substantially along the entire length of the wire between the clamps. The housing can be sized and dimensioned to be positioned within a flow tube of the down hole tool.

In another version of the sensor unit, the clamps are constructed of conductive material. The sensor unit is also provided with an insulating flow tube extending between the clamps. At least one of the clamps is provided with a clamp member, a clamp plate, and at least one fastener connecting the clamp member to the clamp plate so as to clamp the wire between the clamp member and the clamp plate. The clamp member desirably includes an end support connected to the insulating flow tube.

In another aspect, the present invention is directed to a down hole tool which can be positioned in a well bore having a wall and penetrating a subterranean formation having a fluid therein. The down hole tool is provided with a housing, a fluid communication device, and a viscometer. The housing encloses at least one evaluation cavity. The fluid communication device is extendable from the housing for sealing engagement with the wall of the well bore, the fluid communication device has at least one inlet communicating with the evaluation cavity for receiving the fluid from the formation and depositing such fluid into the evaluation cavity. The viscometer is provided with a sensor unit comprising at least two spatially disposed clamps, and a wire suspended in tension between the at least two clamps and positioned within the evaluation cavity such that the wire is available for interaction with the fluid, and at least one magnet emitting a magnetic field interacting with the wire. The sensor unit can be either of the two versions of the sensor units discussed above, for example.

The present invention also relates to a method for determining a viscosity of a fluid within a well bore penetrating a formation having the fluid therein. In the method, a fluid communication device of the down hole tool is positioned in sealing engagement with a wall of the well bore. Fluid is drawn out of the formation and into an evaluation cavity within the down hole tool. Then, the viscosity of the fluid is measured within the evaluation cavity with a viscometer having a wire positioned within the evaluation cavity and suspended between two clamps. The evaluation cavity can be a flow-line or a sample chamber.

BRIEF DESCRIPTION OF THE DRAWINGS

So that the above recited features and advantages of the present invention can be understood in detail, a more particular description of the invention, briefly summarized above, may be had by reference to the embodiments thereof that are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

Presently preferred embodiments of the invention are shown in the above-identified figures and described in detail below. In describing the preferred embodiments, like or identical reference numerals are used to identify common or similar elements. The figures are not necessarily to scale and certain features and certain views of the figures may be shown exaggerated in scale or in schematic in the interest of clarity and conciseness.

DEFINITIONS

Certain terms are defined throughout this description as they are first used, while certain other terms used in this description are defined below:

"Annular" means of, relating to, or forming a ring, i.e., a line, band, or arrangement in the shape of a closed curve such as a circle or an ellipse.

"Contaminated fluid" means fluid that is generally unacceptable for hydrocarbon fluid sampling and/or evaluation because the fluid contains contaminates, such as filtrate from the mud utilized in drilling the borehole.

"Down hole tool" means tools deployed into the well bore by means such as a drill string, wireline, and coiled tubing for performing down hole operations related to the evaluation, production, and/or management of one or more subsurface formations of interest.

"Operatively connected" means directly or indirectly connected for transmitting or conducting information, force, energy, or matter (including fluids).

"Virgin fluid" means subsurface fluid that is sufficiently pure, pristine, connate, uncontaminated or otherwise considered in the fluid sampling and analysis field to be acceptably representative of a given formation for valid hydrocarbon sampling and/or evaluation.

"Fluid" means either "virgin fluid" or "contaminated fluid."

"Clamp" means a device designed to bind or constrict or to press two or more parts together so as to hold them firmly.

DETAILED DESCRIPTION

Figure 1:
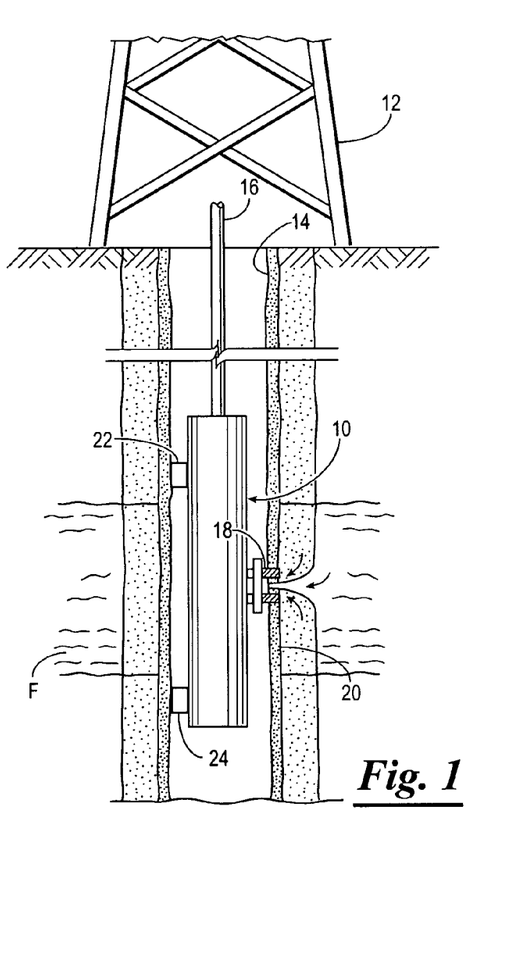
FIG. 1 is a schematic, partial cross-sectional view of a down hole wireline tool having an internal viscometer with the wireline tool suspended from a rig.

FIG. 1 depicts a down hole tool 10 constructed in accordance with the present invention suspended from a rig 12 into a well bore 14. The down hole tool 10 can be any type of tool capable of performing formation evaluation, such as drilling, coiled tubing or other down hole tool. The down hole tool 10 of FIG. 1 is a conventional wireline tool deployed from the rig 12 into the well bore 14 via a wire line cable 16 and positioned adjacent to a formation F. The down hole tool 10 is provided with a probe 18 adapted to seal with a wall 20 of the well bore 14 (hereinafter referred to as a "wall 20" or "well bore wall 20") and draw fluid from the formation F into the down hole tool 10 as depicted by the arrows. Backup pistons 22 and 24 assist in pushing the probe 18 of the down hole tool 10 against the well bore wall 20.

Figure 2:
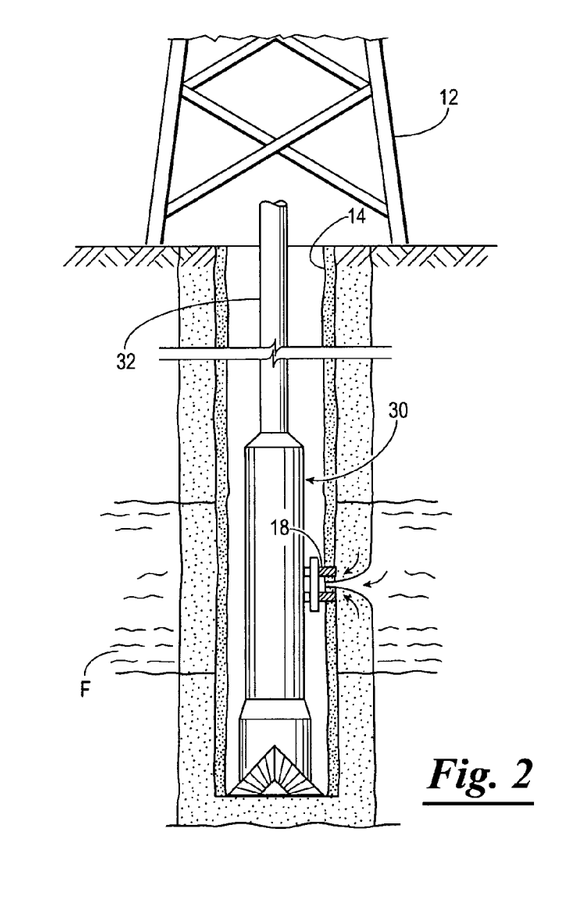
FIG. 2 is a schematic, partial cross-sectional view of a down hole drilling tool having an internal viscometer with the down hole drilling tool suspended from a rig.

FIG. 2 depicts another example of a down hole tool 30 constructed in accordance with the present invention. The down hole tool 30 of FIG. 2 is a drilling tool, which can be conveyed among one or more (or itself may be) a measurement-while-drilling (MWD) drilling tool, a logging-while-drilling (LWD) drilling tool, or other drilling tool that are known to those skilled in the art. The down hole tool 30 is attached to a drill string 32 driven by the rig 12 to form the well bore 14. The down hole tool 30 includes the probe 18 adapted to seal with the wall 20 of the well bore 14 to draw fluid from the formation F into the down hole tool 30 as depicted by the arrows.

Figure 3:
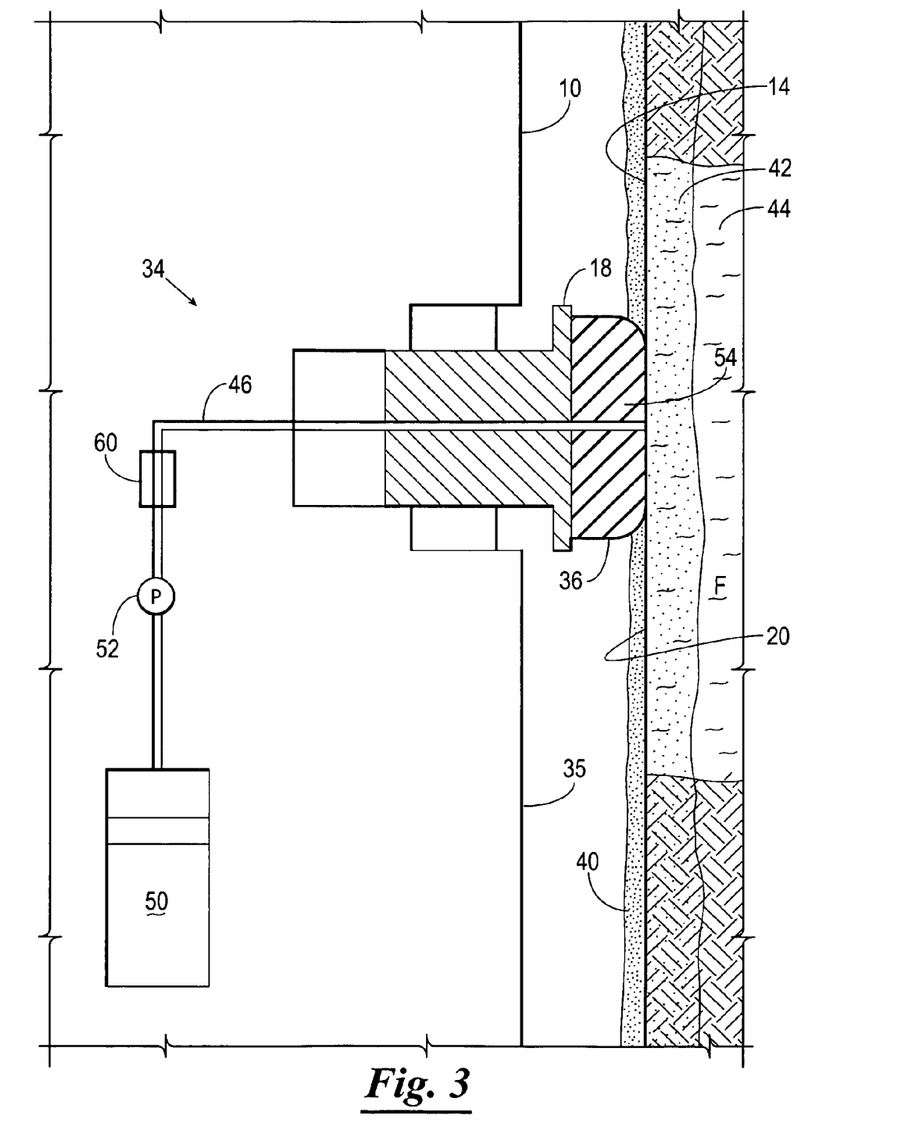
FIG. 3 is a schematic representation of a portion of the downhole tool of FIG. 1 having a probe registered against a sidewall of the well bore and a viscometer positioned within an evaluation flowline within the downhole tool.

FIG. 3 is a schematic view of a portion of the down hole tool 10 of FIG. 1 depicting a fluid flow system 34. The probe 18 is preferably extended from a housing 35 of the down hole tool 10 for engagement with the well bore wall 20. The probe 18 is provided with a packer 36 for sealing with the well bore wall 20. The packer 36 contacts the well bore wall 20 and forms a seal with a mud cake 40 lining the well bore 14. Portions of the mud seep into the well bore wall 20 and creates an invaded zone 42 about the well bore 14. The invaded zone 42 contains mud and other well bore fluids that contaminate the surrounding formations, including the formation F and a portion of the virgin fluid 44 contained therein.

The probe 18 is preferably provided with an evaluation flow line 46. Examples of fluid communication devices, such as probes and dual packers, used for drawing fluid into a flow line are depicted in U.S. Pat. Nos. 4,860,581 and 4,936,139.

The evaluation flowline 46 extends into the down hole tool 10 and is used to pass fluid, such as virgin fluid 44 into the down hole tool 10 for testing and/or sampling. The evaluation flowline 46 extends to a sample chamber 50 for collecting samples of the virgin fluid 44. A pump 52 may be used to draw fluid through the flowline 46.

While FIG. 3 shows a sample configuration of a down hole tool used to draw fluid from a formation, it will be appreciated by one of skill in the art that a variety of configurations of probes, flowlines and down hole tools may be used and is not intended to limit the scope of the invention.

In accordance with the present invention, a viscometer 60 is associated with an evaluation cavity within the down hole tool 10, such as the evaluation flowline 46 for measuring the viscosity of the fluid within the evaluation cavity. The viscometer 60 is shown in more detail in FIGS. 4, 5 and 6.

The down hole tool 30 may also be provided with the housing 35, probe 18, fluid flow system 34, packer 36, evaluation flowline 46, sample chamber 50, pump(s) 52 and viscometer(s) 60 in a similar manner as the down hole tool 10.

Figures 4, 5:
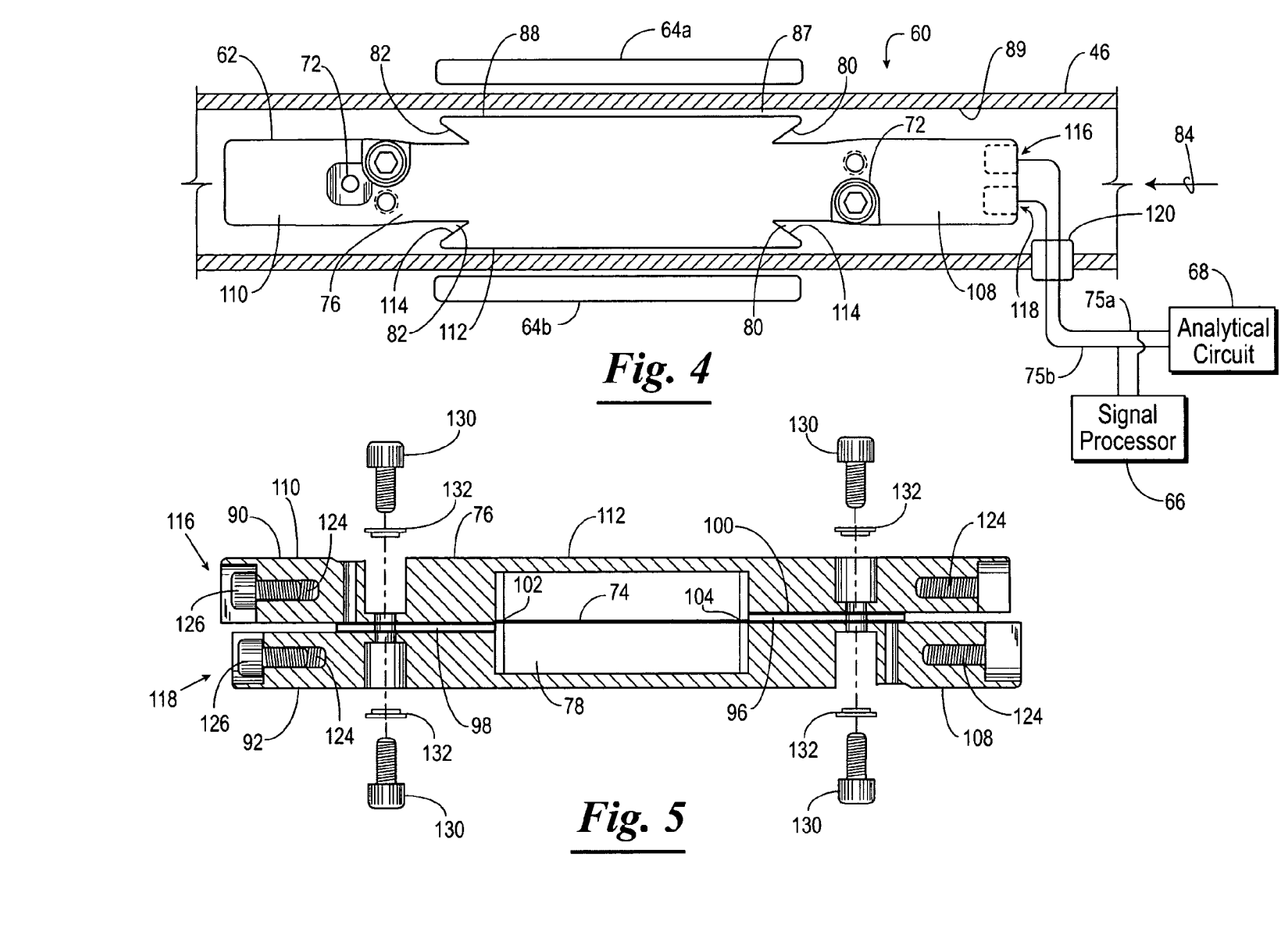
FIG. 4 is a side elevation of a viscometer positioned within an evaluation cavity.
FIG. 5 is a cross-sectional view of a sensor unit of the viscometer of FIG. 4 showing a suspended wire.
Figure 6A:
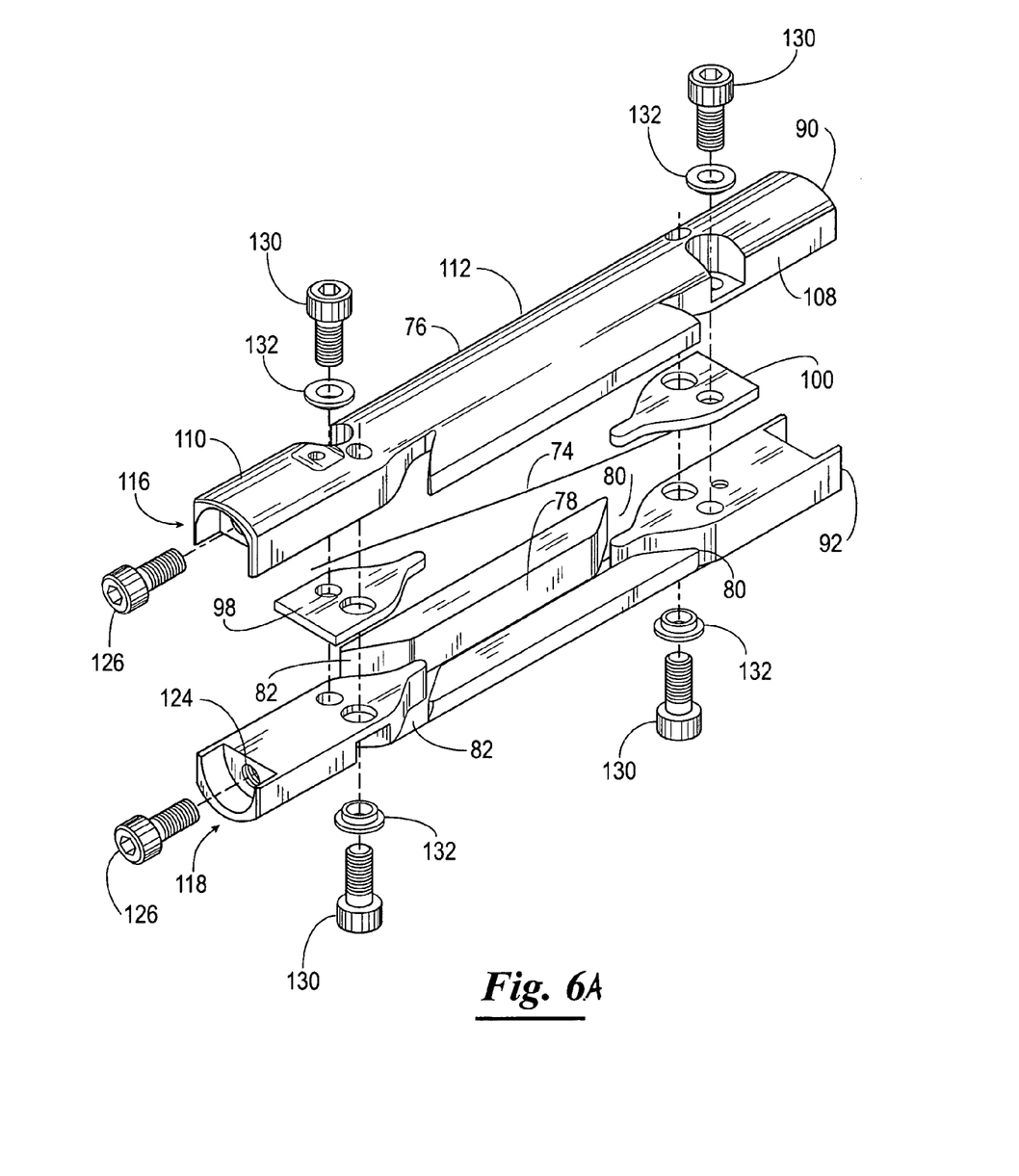
FIG. 6A is an exploded perspective view of the sensor unit of the viscometer depicted in FIG. 4.
Figure 6B:
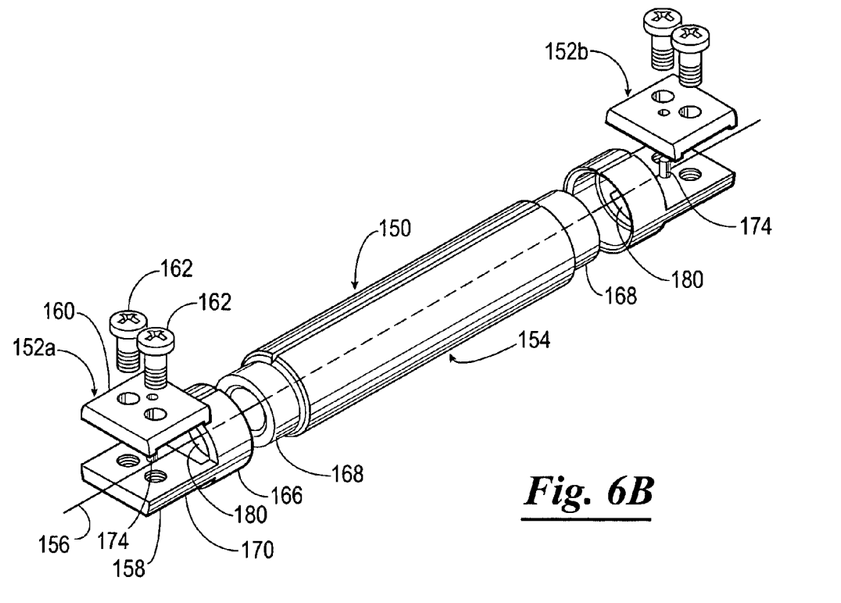
FIG. 6B is an exploded perspective view of another sensor unit of a viscometer.
Figure 7:
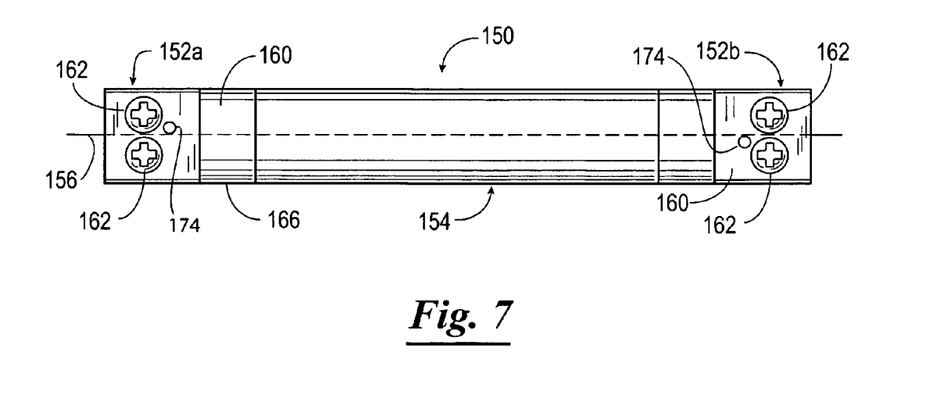
FIG. 7 is a top plan view of the sensor unit depicted in FIG. 6B.

Referring now to FIGS. 4-6, the viscometer 60 will be described in detail hereinafter with respect to the evaluation cavity being within the evaluation flowline 46. However, it should be understood that the following description is equally applicable to the evaluation cavity being within the sample chamber 50. It should also be understood that although the viscometer 60 will be described in conjunction with the down hole tool 10, such description is equally applicable to the down hole tool 30. Moreover, while the viscometer 60 is depicted in FIG. 3 positioned along flowlines 46, the viscometer 60 may be positioned in various locations about the down hole tool 10 for measuring down hole parameters.

In general, the viscometer 60 has a sensor unit 62, one or more magnets 64(*a, b*), a signal processor 66, and an analytical circuit 68. In the example shown in FIG. 4, the viscometer 60 is provided with two magnets which are designated in FIG. 4 by the reference numerals 64*a* and 64*b*. The sensor unit 62 is provided with at least two spatially disposed clamps 72, and a wire 74 (FIG. 5) suspended between the least two clamps 72 such that the wire 74 is available for interaction with the fluid when the sensor unit 62 of the viscometer 60 is positioned within the down hole tool 10 and the down hole tool 10 is positioned within the subterranean formation F and receives the fluid from the formation F. The magnets 64*a* and 64*b* emit a magnetic field, which interacts with the sinusoidal current flowing through the wire 74. The signal processor 66 electrically communicates with the wire 74 via signal paths 75*a* and 75*b*. The signal paths 75*a* and 75*b* can be wire, cable or air-way communication links. The signal processor 66 provides a drive voltage forming a sinusoidal current to the wire 74, which typically causes the wire 74 to vibrate or resonate consistent with the signal provided thereto. Typically, the signal provided to the wire 74 from the signal processor 66 can be considered a swept frequency constant current signal wherein the frequency of the signal is changing in a predetermined manner.

The analytical circuit 68 receives feedback from the wire 74. The sinusoidal current flows through the wire 74 and when the frequency is close to that of a resonance, typically the lowest order mode, a detectable motional electromotive force ("emf") is generated. It is the drive voltage and the motional emf that are measured as a function of frequency over the resonance. Typically, the analytical circuit 68 receives feedback from the wire 74 indicative of the resonant frequency of the wire 74. Depending upon the viscosity of the fluid, the resonant frequency of the wire 74 changes in a predictable manner, which allows for the determination of the viscosity of the fluid. The manner in which the viscosity is determined from the feedback from the wire 74 will be discussed in more detail below. The analytical circuit 68 can be any type of circuit capable of receiving feedback from the wire 74 and calculating the viscosity of the fluid. Typically, the analytical circuit 68 will include a computer processor executing a software program for permitting the analytical circuit 68 to calculate the viscosity. However, it should be understood that in certain embodiments, the analytical circuit 68 could be implemented using analog, or other types of devices. For example, the analytical circuit 68 may include an analog-to-digital converter followed by a decoder for calculating the viscosity of the fluid. Although the analytical circuit 68 and signal processor 66 have been shown in FIG. 4 separately, it should be understood that the analytical circuit 68 and the signal processor 66 can be implemented in a single circuit, or implemented in separate circuits. Furthermore, although the analytical circuit 68 and the signal processor 66 are illustrated in FIG. 4 as being within the down hole tool 10, it should be understood that the signal processor 66 and/or the analytical circuit 68 could be located external to the down hole tool 10. For example, the signal processor 66 for generating the swept signal can be located within the down hole tool 10, while the analytical circuit 68 is located outside of the well bore 14 in a monitoring center located either near the well bore 14 or remote from the well bore 14.

The sensor unit 62 of the viscometer 60 is also provided with a housing 76. The housing 76 defines a channel 78 (FIGS. 5 and 6), an inlet 80 communicating with the channel 78, and an outlet 82 communicating with the channel 78. In the example depicted in FIG. 4, the fluid is flowing in a direction 84 through the evaluation flow line 46. Thus, when the fluid encounters the sensor unit 62, the fluid flows through the inlet 80, into the channel 78 and exits the housing 76 through the outlet 82. When the housing 76 is provided with an outer dimension smaller than an inner dimension of the evaluation flowline 46, a certain amount of the fluid will also flow past the housing 76 in a channel 87 (FIG. 4) formed between an outer surface 88 of the housing 76, and an inner surface 89 of the evaluation flowline 46.

The wire 74 is positioned within the channel 78 so that the fluid will come into contact with substantially the entire wire 74 between the clamps 72 as the fluid passes through the housing 76. This ensures that the fluid flows over the entire length of the wire 74 between the clamps 72 to facilitate cleaning the wire 74 between fluids. The wire 74 is constructed of a conductive material capable of vibrating at a plurality of resonant frequencies depending upon the tension of the wire 74 and the viscosity of the fluid surrounding the wire 74. The wire 74 is desirably constructed of a material having a large density because the greater the difference in density of the wire 74 to that of the fluid the greater the sensitivity. The wire 74 also needs to have a high Young's modulus to provide a stable resonance while the density provides sensitivity to the fluid around it, through the ratio of the density of the fluid/the density of the wire. The wire 74 can be constructed of dense material, such as tungsten.

As shown in FIG. 4, the magnets 64 are preferably positioned on the exterior of the evaluation flowline 46 and mounted to an exterior surface of the evaluation flowline 46.

As shown in FIGS. 5 and 6, the housing 76 may be provided with a first housing member 90 and a second housing member 92. The first housing member 90 and the second housing member 92 cooperate to define the channel 78. The first housing member 90 and the second housing member 92 are preferably constructed of a conductive, non-magnetic material such that the magnetic field generated by the magnets 64 can interact with the wire 74 without substantial interference from the housing 76. For example, the first housing member 90 and the second housing member 92 may be constructed of a down hole compatible material, such as K500 Monel or other type of non-magnetic material, e.g., stainless steel.

The housing 76 is also provided with an insulating layer 96 (FIG. 5) positioned between the first housing member 90 and the second housing member 92 so as to electrically isolate the first housing member 90 from the second housing member 92. The wire 74 extends between opposite sides of the insulating layer 96 to electrically connect the first housing member 90 to the second housing member 92. The insulating layer 96 may be constructed of a first insulating member 98, and a second insulating member 100. The wire 74 is provided with a first end 102, and a second end 104. The first insulating member 98 is positioned adjacent to the first end 102 of the wire 74, and the second insulating member 100 is positioned adjacent to the second end 104 of the wire 74. The wire 74 spans the channel 78 and serves to electrically connect the first housing member 90 to the second housing member 92.

In the example of the sensor unit 62 depicted in FIG. 4, each of the first housing member 90 and the second housing member 92 can be characterized as having a first end portion 108, a second end portion 110, and a medial portion 112 positioned between the first end portion 108 and the second end portion 110. The first end portion 108 and the second end portion 110 are provided with a cross-sectional area, or diameter which is less than a cross-sectional area or diameter of the medial portion 112. Thus, each of the first housing member 90, and the second housing member 92 has a shoulder 114 separating the first end portion 108 and the second end portion 110 from the medial portion 112. The inlet 80 and the outlet 82 are defined in the first housing member 90 and the second housing member 92 proximate to the shoulders 114 such that the channel 78 extends through the medial portion 112 of the housing 76. The shoulders 114 are shaped to direct the fluid into the inlet 80.

To connect the signal paths 75*a* and 75*b* to the sensor unit 62, the viscometer 60 is further provided with a first terminal 116 coupled to the first housing member 90 and a second terminal 118 coupled to the second housing member 92. The signal processor 66 and the analytical circuit 68 are thus in communication with the first and second terminals 116 and 118 via the signal paths 75*a* and 75*b*. It should be noted that the signal paths 75*a* and 75*b* typically extend through the evaluation flowline 46 via one or more feed-throughs 120. The feed-throughs 120 provide a fluid tight seal to permit the signal paths 75*a* and 75*b* to extend through the evaluation flowline 46 while preventing fluid from flowing through the opening formed in the evaluation flowline 46.

The first terminal 116 and the second terminal 118 may be identical in construction and function. To implement the first terminal 116 and the second terminal 118, the first housing member 90 and the second housing member 92 can be provided with threaded holes 124 formed in either the first end portion 108 or the second end portion 110 of the first housing member 90 and the second housing member 92. In the example depicted in FIG. 5, the first housing member 90 and the second housing member 92 are provided with the threaded holes 124 formed in both the first end portion 108 and the second end portion 110 thereof. As depicted in FIGS. 4-6, the first terminal 116 and the second terminal 118 are also provided with threaded fasteners 126 to connect each of the signal paths 75*a* and 75*b* to the first housing member 90 and the second housing member 92.

The first housing member 90 and the second housing member 92 are connected together by way of any suitable mechanical or chemical type assembly. As depicted in FIG. 6, the viscometer 60 is provided with a plurality of threaded fasteners 130 (FIG. 6) for securing the first housing member 90 to the second housing member 92. It should be noted that the threaded fasteners 130 are typically constructed of conductive materials, such as steel or aluminum. To prevent the threaded fasteners 130 from forming electrical paths between the first housing member 90 and the second housing member 92, the viscometer 60 is also provided with a plurality of electrically insulated feed-throughs 132 to electrically isolate each of the threaded fasteners 130 from one of the corresponding first housing member 90 and the second housing member 92.

The sensor unit 62 of the viscometer 60 can be anchored within the evaluation flow line 46 by any suitable assembly. It should be understood that the sensor unit 62 should be anchored to prevent longitudinal movement within the evaluation flow line 46 and rotational movement within the evaluation flow line 46. The signal paths 75*a* and 75*b* are preferably provided with sufficient rigidity to prevent longitudinal and/or rotational movement of the sensor unit 62 within the evaluation flow line 46. Further anchoring means can also be used to prevent movement of the sensor unit 62 within the evaluation flow line 46. For example, the evaluation flow line 46 can be necked-down downstream of the sensor unit 62 so as to prevent longitudinal movement of the sensor unit 62 within the evaluation flowline 46.

As will be understood by one skilled in the art, the first housing member 90 and the second housing member 92, when secured together by way of the threaded fasteners 130, cooperate to form the clamps 72. The wire 74 is clamped and tensioned as follows. The wire 74 is clamped at one end. The other end is fed through the second clamp 72 but which is not tightened. A mass (not shown) is attached from the end protruding from the loose clamp 72. The magnitude of the mass, which hangs from the wire 74 within the Earth's gravitational field, determines the tension for a wire diameter and therefore the resonance frequency; a resonance frequency of about 1 kHz can be obtained with a mass of 500 g suspended on a wire of diameter 0.1 mm. After about 24 h, the wire 74 is clamped at the second end and the mass removed. This procedure reduces the twist within the wire 74. The wire 74 is then heated and cooled so as to produce a wire with a resonance frequency that is reasonably stable between each thermal cycle; for the viscometer 60, the wire 74 resonance frequency needs to be stable during the time required to determine the complex voltage as a function of frequency over the resonance which is on the order of 60 s.

To calculate the viscosity, a sinusoidal current is fedthrough the wire 74 in the presence of a magnetic field. The magnetic field is perpendicular to the wire 74 and in the presence of the sinusoidal current causes the wire 74 to move. The resulting induced electromotive force (motional emf) or complex voltage is added to the driving voltage. The motional emf can be detected via the analytical circuit 68 with signal processors that include lock-in amplifiers, where the driving voltage can be offset or rendered null, or spectrum analyzers. When the frequency of the current is close to or at that of the fundamental resonance frequency the wire 74 resonates. The complex voltage is usually measured at frequencies over the resonance and the observations combined with the working equations, wire density and radius, to determine the viscosity for a fluid of known density. The magnitude of the current depends on the viscosity of the fluid and is varied so that an acceptable signal-to-noise ratio is obtained with the detection circuitry; values less than 35 mA are typically used and the resulting complex motional emf of a few microvolts. In addition to the magnitude of the current the diameter of the wire 74 also determines the upper operating viscosity; increasing the wire diameter increases the upper operating viscosity. There are other ways of exciting and detecting wire motion but none so convenient as a lock-in amplifier.

Shown in FIG. 6B is another version of a sensor unit 150 for use with the viscometer 60. As will be discussed in more detail below, the sensor unit 150 is similar in construction and function as the sensor unit 62 described above, with the exception that the sensor unit 150 is provided with a pair of conductive clamps 152 separated by an electrically insulated flow tube 154 surrounding a wire 156, rather than having the conductive first housing member 90 and second housing member 92 separated by a parallel extending electrically insulated layer 96. The sensor unit 150 will be described in more detail below.

The clamps 152 are designated in FIG. 6B by way of the reference numerals 152a and 152b for purposes of clarity. The clamps 152 are identical in construction and function. Thus, only the clamp 152a will be described hereinafter. The clamp 152a is provided with a clamp member 158, a clamp plate 160, and at least one fastener 162 for connecting the clamp plate 160 to the clamp member 158. The clamp member 158 is connected to the flow tube 154 via any suitable mating assembly. For example, as shown in FIG. 6B the clamp member 158 is provided with an end support 166 that mates with a predetermined portion of the flow tube 154 such that the end support 166 is supported by the flow tube 154. In the version depicted in FIG. 6B, the flow tube 154 is provided with a necked down portion 168, and the end support 166 defines a collar positioned over the necked down portion 168. The clamp member 158 is also provided with a flange 170 connected to and extending from the end support 166. To center the wire 156 on the flange 170, at least one registration pin 174 is provided on the flange 170. Desirably, the clamp member 158 is provided with at least two spaced-apart registration pins 174 such that the wire 156 can be threaded between the registration pins 174 as shown in FIG. 6B.

The fasteners 162 connect the clamp plate 160 to the clamp member 158 so as to clamp the wire 156 thereto. The fasteners 162 can be any type of device capable of connecting the clamp member 158 to the clamp plate 160. For example, the fastener 162 can be a screw.

The flow tube 154 is preferably constructed of a material which has a similar coefficient of thermal expansion as the wire 156. When the wire 156 is constructed of tungsten, the flow tube 154 can be constructed of Shapal-M, a ceramic.

At least one opening 180 is formed in the clamp member 158 to permit fluid to enter or exit the flow tube 154 through the opening 180. As shown in FIG. 6B, the clamp member 158 can be provided with at least two openings 180 with each opening 180 having a semicircular shape. However, it should be understood that the shape of the openings 180 can vary depending on the desires of the designer. More specifically, it should be understood that the openings 180 can have any asymmetrical, symmetrical or fanciful shape.

The wire 156 is constructed in a similar manner to the wire 74 discussed above. The wire 156 is supported and tensioned within the flow tube 154 in a similar manner as the wire 74 is supported and tensioned within the housing 76. The signal paths 75a and 75b from the signal processor 66 and the analytical circuit 68 are connected to the respective clamps 152 in any suitable manner, such as screws, bolts, terminals or the like.

It will be understood from the foregoing description that various modifications and changes may be made in the preferred and alternative embodiments of the present invention without departing from its true spirit. The devices included herein may be manually and/or automatically activated to perform the desired operation. The activation may be performed as desired and/or based on data generated, conditions detected and/or analysis of results from down hole operations.

This description is intended for purposes of illustration only and should not be construed in a limiting sense. The scope of this invention should be determined only by the language of the claims that follow. The term "comprising" within the claims is intended to mean "including at least" such that the recited listing of elements in a claim are an open group. "A," "an" and other singular terms are intended to include the plural forms thereof unless specifically excluded.

What is claimed is:

1. A viscometer for a down hole tool positionable in a well bore penetrating a subterranean formation, the down hole tool adapted to convey at least a portion of a fluid in the formation to the viscometer, the viscometer comprising:
   a sensor unit positionable within the down hole tool, the sensor unit comprising:
   at least two spatially disposed clamps;
   a wire suspended in tension between the at least two clamps such that the wire is available for interaction with the fluid when the viscometer is positioned within the down hole tool and the down hole tool is positioned within the subterranean formation and receives the fluid from the subterranean formation; and
   at least one magnet emitting a magnetic field interacting with the wire.

2. The viscometer of claim 1, further comprising a signal processor in electrical communication with the wire for providing a signal to the wire, an analytical circuit receiving feedback from the wire for determining the viscosity of the fluid when the viscometer is positioned within the down hole tool and the down hole tool is positioned within the subterranean formation and receives the fluid from the formation.

3. The viscometer of claim 1, wherein the sensor unit further comprises a housing defining a channel and an inlet communicating with the channel, and wherein the wire is positioned within the channel.

4. The viscometer of claim 3, wherein the housing comprises a first housing member and a second housing member with the first housing member and the second housing member cooperating to define the channel.

5. The viscometer of claim 4, wherein the first housing member and the second housing member are constructed of at least one conductive, non-magnetic material.

6. The viscometer of claim 5, wherein the housing further comprises an insulating layer positioned between the first housing member and the second housing member so as to electrically isolate the first housing member from the second housing member.

7. The viscometer of claim 6, further comprising a first terminal coupled to the first housing member, and a second terminal coupled to the second housing member, and wherein the signal processor and the analytical circuit are in electrical communication with the first and second terminals.

8. The viscometer of claim 3, wherein the housing is sized and dimensioned to be positioned within a flow tube of the down hole tool.

9. The viscometer of claim 4, wherein the first housing member and the second housing member cooperate to form the clamps.

10. The viscometer of claim 3, wherein the channel extends substantially along the entire length of the wire between the clamps.

11. The viscometer of claim 1, wherein the clamps are constructed of conductive material, and wherein the sensor unit further comprises an electrically insulated flow tube extending between the clamps.

12. The viscometer of claim 11, wherein at least one of the clamps comprises:
   a clamp member;
   a clamp plate; and
   at least one fastener connecting the clamp member to the clamp plate so as to clamp the wire between the clamp member and the clamp plate.

13. The viscometer of claim 12, wherein the clamp member comprises an end support connected to the electrically insulated flow tube.

14. The viscometer of claim 12, wherein the end support defines a collar positioned on an end of the electrically insulated flow tube.

15. A down hole tool positionable in a well bore having a wall and penetrating a subterranean formation, the formation having a fluid therein, the down hole tool comprising:
   a housing enclosing at least one evaluation cavity;
   a fluid communication device extendable from the housing for sealing engagement with the wall of the well bore, the fluid communication device having at least one inlet communicating with the evaluation cavity for receiving the fluid from the formation and depositing such fluid into the evaluation cavity; and
   a viscometer comprising:
      a sensor unit comprising:
         at least two spatially disposed clamps; and
         a wire suspended in tension between the at least two clamps and positioned within the evaluation cavity such that the wire is available for interaction with the fluid; and
      at least one magnet emitting a magnetic field interacting with the wire.

16. The down hole tool of claim 15, wherein the viscometer further comprises:
   a signal processor in electrical communication with the wire for providing a signal to the wire; and
   an analytical circuit receiving feedback from the wire for determining the viscosity of the fluid when the viscometer is positioned within the down hole tool and the down hole tool is positioned within the subterranean formation and receives the fluid.

17. The down hole tool of claim 15, wherein the sensor unit of the viscometer further comprises a housing defining a channel and an inlet communicating with the channel, and wherein the wire is positioned within the channel.

18. The down hole tool of claim 17, wherein the housing of the viscometer comprises a first housing member and a second housing member with the first housing member and the second housing member cooperating to define the channel.

19. The down hole tool of claim 18, wherein the first housing member and the second housing member are constructed of a conductive, non-magnetic material.

20. The down hole tool of claim 18, wherein the housing of the viscometer further comprises an insulating layer positioned between the first housing member and the second housing member so as to electrically isolate the first housing member from the second housing member.

21. The down hole tool of claim 18, wherein the first housing member and the second housing member cooperate to form the clamps.

22. The down hole tool of claim 15, wherein the evaluation cavity is defined by a flow-line.

23. The down hole tool of claim 22, wherein the flow line is an evaluation flow line.

24. The down hole tool of claim 15, wherein the evaluation cavity is defined by a sample chamber.

25. The down hole tool of claim 17, wherein the channel extends substantially along the entire length of the wire between the clamps.

26. The downhole tool of claim 15, wherein the clamps are constructed of conductive material, and wherein the sensor unit further comprises an electrically insulated flow tube extending between the clamps.

27. The downhole tool of claim 26, wherein at least one of the clamps comprises:
   a clamp member;
   a clamp plate; and
   at least one fastener connecting the clamp member to the clamp plate so as to clamp the wire between the clamp member and the clamp plate.

28. The downhole tool of claim 27, wherein the clamp member comprises an end support connected to the electrically insulated flow tube.

29. The downhole tool of claim 28, wherein the end support defines a collar positioned on an end of the electrically insulated flow tube.

30. A method for determining a viscosity of a fluid within a well bore penetrating a formation having the fluid therein, comprising the steps of:

positioning a fluid communication device of the down hole tool in sealing engagement with a wall of the well bore;

drawing fluid out of the formation and into an evaluation cavity within the down hole tool; and measuring the viscosity of the fluid within the evaluation cavity with a viscometer having a wire positioned within the evaluation cavity and suspended between two clamps.

31. The method of claim 30 wherein the evaluation cavity is a flow-line.

32. The method of claim 30 wherein the evaluation cavity is a sample chamber.

* * * * *